US005430306A

United States Patent [19]
Ix

[11] Patent Number: 5,430,306
[45] Date of Patent: Jul. 4, 1995

[54] OPTOELECTRONIC DETECTOR WITH HIGH, UNIFORM SENSITIVITY AND LARGE FIELD OF VIEW, FOR THERMAL-INKJET INKDROPS

[75] Inventor: Hanno Ix, Escondido, Calif.

[73] Assignee: Hewlett-Packard Company, Palo Alto, Calif.

[21] Appl. No.: 177,085

[22] Filed: Jan. 3, 1994

[51] Int. Cl.⁶ .............................................. G01D 15/18
[52] U.S. Cl. .................................. 250/573; 250/222.2;
347/6; 347/19; 347/81
[58] Field of Search ............. 250/573, 574, 221, 222.1,
250/222.2; 347/81, 78, 12, 13, 14, 19, 6, 51;
73/861.41; 356/335, 336, 337, 338

[56] References Cited

U.S. PATENT DOCUMENTS

| | | | |
|---|---|---|---|
| 4,318,482 | 3/1982 | Barri et al. | 250/222.2 |
| 4,550,322 | 10/1985 | Tamai | 347/81 |
| 4,754,289 | 6/1988 | Kudo | 347/81 |
| 4,835,435 | 5/1989 | Yeung et al. | 347/6 |
| 4,922,268 | 5/1990 | Osborne | 347/19 |
| 4,922,270 | 5/1990 | Cobbs et al. | 347/19 |
| 5,304,814 | 4/1994 | Markham | 347/6 |

*Primary Examiner*—David C. Nelms
*Assistant Examiner*—John R. Lee

[57] ABSTRACT

The device ascertains existence of a small inkdrop to be ejected from a thermal-inkjet pen. It includes a light source (preferably a nonpoint source with extended threadlike form perpendicular to the light path), detector, and optical element—preferably a cylindrical lens—for passing light from source to detector through an inkdrop probe volume, and for causing that light to be concentrated near the detector. Along a segment of the light path near the detector, the light is concentrated into a cross-section which is much smaller than that of the probe volume and is, within that segment, approximately independent of position along the path. The detector intersects the light within that segment; both the light beam within that segment and the detector have elongated, narrow shapes transverse to the light path, with regions in which brightness and sensitivity are approximately independent of position along the elongated shapes, and which are mutually crossed within these regions—so that positioning of the detector need not be precise in any direction. The apparatus has provision for firing an inkdrop through the probe volume, from a thermal-inkjet pen. Preferably the device is made for use with two or several different thermal-inkjet pens, each having a respective array of nozzles for ejecting such inkdrops; the several pens include some that have different nozzle-array footprints; and the probe volume accommodates drops ejected through all the different footprints. Analysis of the system detection sensitivity reveals a controllable variation with respect to drop position within the probe volume—including at least one constant-sensitivity contour. Preferably the inkdrops pass along at least one of the constant-sensitivity contours.

26 Claims, 8 Drawing Sheets

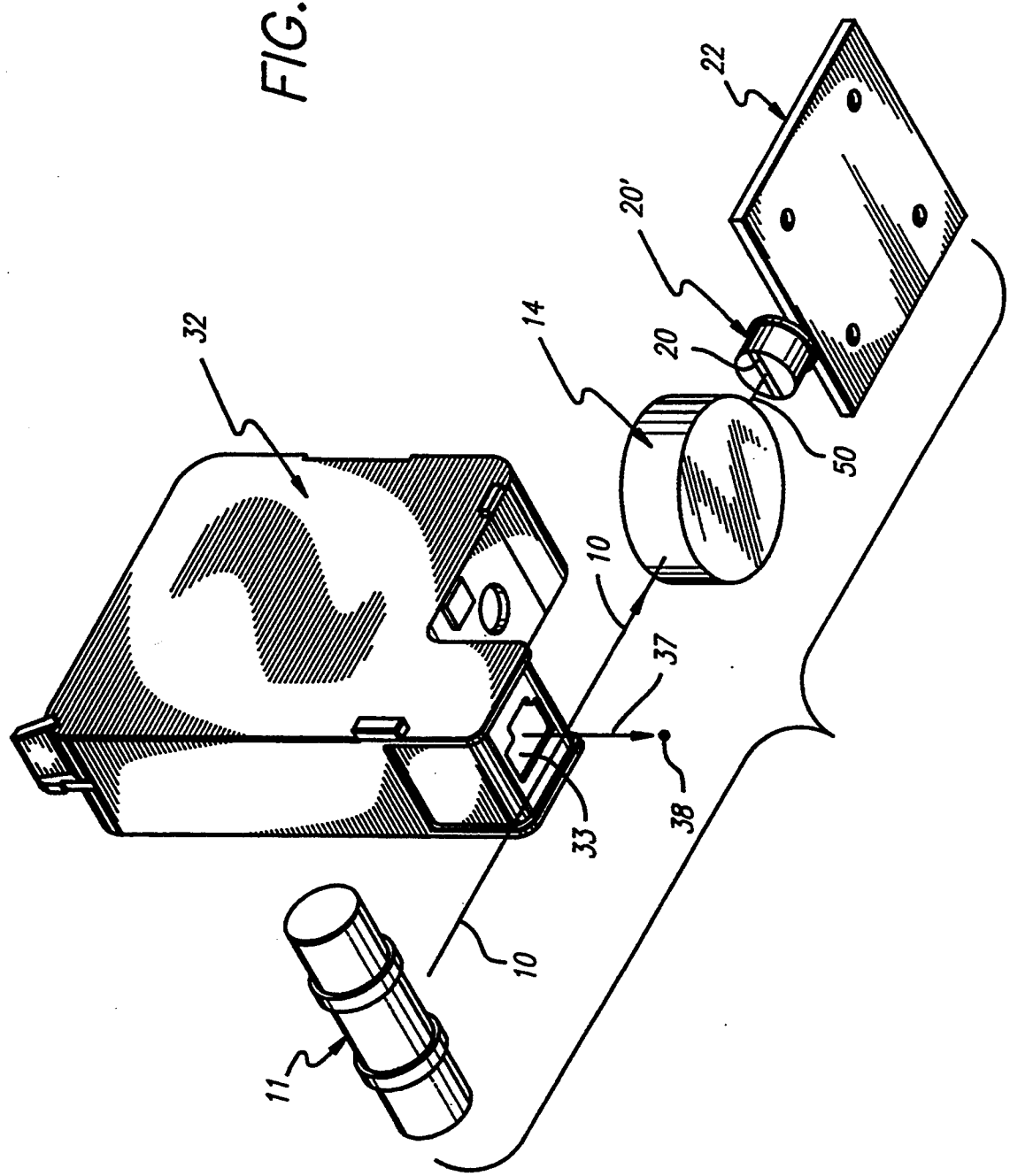

OPTOELECTRONIC DETECTOR WITH HIGH, UNIFORM SENSITIVITY AND LARGE FIELD OF VIEW, FOR THERMAL-INKJET INKDROPS

RELATED PATENT DOCUMENTS

Coowned U.S. utility-patent application Ser. No. 08/056,011, which was filed in the name of Lowell Stewart on Apr. 30, 1993, includes subject matter related to that of the present document and is hereby incorporated in its entirety into this document by reference.

BACKGROUND

1. FIELD OF THE INVENTION

This invention relates generally to thermal-inkjet printing systems; and more particularly to apparatus and methods for ascertaining whether very small inkdrops have been ejected by thermal-inkjet pens. As will be described below, however, some such apparatus and methods have application to detecting other types of particles in other kinds of systems.

2. RELATED ART

Inkdrop detectors are useful in thermal-inkjet printing machines to ascertain whether an inkdrop exists, after an ink-ejection nozzle has been commanded to produce one. In this way these devices can verify that each ink-ejection nozzle or particular ink-ejection nozzles are operating properly, or can initiate corrective actions in event one or more nozzles is not operating properly, or can be used (as in coowned U.S. Pat. Nos. 4,922,268 of Osborne, and 4,922,270 of Cobbs, Haselby and Osborne) to calibrate the nozzle or pen position relative to other parts of the printing machine.

Coowned U.S. Pat. No. 4,835,435 of Yeung and Franz describes the art prior to 1988 in such printers and in other contexts. That patent, however—based on an assumption that optical detection systems necessarily require difficult, expensive optical alignments—proposes a detection system that is percussive, employing a piezoelectric membrane to develop an electrical signal in response to inkdrop impingement.

The resulting system works well for its intended purposes, but cannot be made sensitive enough for present and future thermal-inkjet printers. Indeed the size of inkdrops in such printers will decrease as this technology advances and the desired spatial resolution (number of addressable locations) becomes ever finer. Moreover, piezoelectric drop detectors have a drawback: ink must be cleaned from the sensitive surface at least occasionally.

Earlier optoelectronic drop detectors, such as that of Cobbs et al. mentioned above, similarly work well for droplets of 45 pL or more and in the '270 patent cover a field of view of about 0.15 by 2½ cm (0.06 by 1 inch). Present-day pens, however, generate inkdrops about one order of magnitude smaller than that.

To maximize printer throughput with fine resolution it is desirable to make pens with a relatively very large number of nozzles; some modern pens accordingly have several hundred nozzles. In many or most designs the nozzles are arranged in two parallel columns, about a quarter-centimeter (tenth-inch) apart and each about 1¼ cm (one-half-inch) long.

The area circumscribing these columns is about 100,000 times the cross-section of an individual drop, but it is desirable that a detection device respond adequately to the presence of a single drop anywhere within such a large envelope—and be highly insensitive to the location of the drop. That is to say, for modern purposes an inkdrop detector must satisfy somewhat contradictory-seeming objectives of sensitivity high enough for a 4½ pL drop but uniform response over a detection area corresponding to the shape and dimensions of the pen nozzle array.

These requirements are compounded by the desirability of providing a single detection device that can be used with a great variety of different pens and thus of nozzle arrays. Many different pens are designed into respective different printers, and in some cases two or more different pens are used in a single printer—even at the same time. For instance a printer may have one relatively small pen for firing only black ink, and a relatively larger pen with three nozzle sets or subarrays, each subarray loaded with ink of a different color respectively.

For modern small-volume inkdrops, especially in large detection envelopes over which uniformity of response is desired as mentioned above, drop-detection signals are extremely small. These signals are corrupted by noise from several sources—including the electromagnetic environment, stray light, and random variations of the drop-generation process—all adding to the difficulty of using inkdrop detectors to ascertain quickly and reliably whether individual nozzles are operating properly.

It can now be seen that prior inkdrop-detection devices, while serviceable for their design objectives, in very important ways leave room for refinement due to the more-demanding context of higher-resolution printers.

SUMMARY OF THE DISCLOSURE

The present invention introduces such refinement. The invention has several major aspects or facets that can be used independently, although for greatest enjoyment of the benefits of the invention they are optimally practiced together.

In preferred embodiments of a first of these primary facets or aspects, the invention is an apparatus for ascertaining existence of a small inkdrop ejected from a thermal-inkjet pen. The apparatus includes a light source, and a detector for receiving light through the light path from the source—and in response thereto generating a corresponding electrical signal.

In addition the apparatus includes means for passing light from the source to the detector through one volume of space which I shall call an inkdrop "probe volume"—and for causing light that passes through the inkdrop probe volume to also be concentrated for passage through another volume of space which I shall call a "beam volume". For purposes of generality and breadth in discussion of my invention, I shall refer to these means simply as the "light-passing-and-concentration-causing means" or sometimes "light-passing-and-concentrating means".

The beam volume lies along a segment of the light path, and has a cross-section that is much smaller than the cross-section of the probe volume; within at least that segment, the beam-volume cross-section is approximately independent of position along the light path. The detector is disposed to intersect the beam volume within that same segment of the light path.

The apparatus also includes some means for firing through the probe volume, from such a thermal-inkjet pen, an inkdrop whose existence is to be ascertained. Again for purposes of generality and breadth I shall refer to these means as the "firing means".

The foregoing may constitute a description or definition of the first major aspect or facet of the invention in its broadest or most general form. Even in this general form, however, this first facet of the invention can be seen to provide important advantages over the prior art.

One of these advantages is that, with straightforward design implementation, inkdrops passing through any part of a relatively large probe volume can be made to have substantially the same geometrical occultation effect at the sensitive surface of a quite small optoelectronic detector. Another advantage is that the described characteristic of the beam volume as it lies along the light path—when properly exploited by simple good mechanical design practice—implies that performance can be made to depend very little upon accuracy of detector alignment with respect to the longitudinal direction along the path.

In preferred embodiments of a second main facet or aspect, the invention is apparatus for ascertaining existence of a small inkdrop. The apparatus includes a plurality of thermal-inkjet pens, each having a respective array of nozzles for ejecting such inkdrops. More particularly the plurality of pens includes pens having a corresponding plurality of different nozzle-array footprints.

The apparatus also includes a light source, and a detector for receiving light through the light path from the source—and, in response to that received light, generating a corresponding electrical signal.

Further the apparatus includes light-passing-and-concentration-causing means as described in relation to the first main facet of the invention, which concentrate light from the probe volume into a smaller beam volume whose cross-section, along a segment of the light path, is approximately independent of position along the path.

Also as in the first facet of the invention, the detector is disposed to intersect the beam volume within that segment; and the apparatus includes means for firing through the probe volume, from at least one of the thermal-inkjet pens, an inkdrop whose existence is to be ascertained.

In this second major aspect or facet of the invention, the inkdrop probe volume has a section through which the firing means cause inkdrops to be fired. By a "section" I mean a geometrical section through the probe volume.

Such a section in principle may be a longitudinal (i.e., lengthwise with respect to the optical path) section through the probe volume, or a cross-section through the probe volume, or indeed a section which is skewed or angled relative to the optical path, but passes through the probe volume. Any such section by its nature has the characteristics of an area.

In this second aspect of the invention, the section exceeds an area that encompasses all nozzles of each one of the plurality of thermal-inkjet pens. By this I mean that the section has a shape and size large enough to accept inkdrops fired from all the nozzles of any one of the pens, without relative motion of that pen and the section.

Once again the foregoing paragraphs may constitute a definition or description of the second main facet of my invention in its most general or broad form. Even in this form the invention can be seen to importantly advance the art—and particularly the economics—of inkdrop detectors, because:

a single apparatus design can be manufactured in quantity, and the resulting units used for installation in any one of a great variety of different printers—even though these printers respectively utilize a corresponding variety of different pens with different nozzle-array footprints; and a single unit of the same apparatus design can be installed in a single printer which simultaneously uses two or more pens having different footprints.

In a third of its major aspects or facets, the invention is apparatus for ascertaining existence of a small inkdrop ejected from a thermal-inkjet pen. The apparatus includes a light source, and a detector for receiving light through the light path from the source—and in response thereto generating a corresponding electrical signal.

This apparatus also includes some means for cooperating with the source to define an inkdrop probe volume. Once again for generality and breadth I shall call these means the "probe-volume defining means".

In this apparatus, sensitivity of the above-mentioned electrical signal to inkdrop existence is variable with respect to inkdrop position within the probe volume. The probe-volume defining means, however, establish within the probe volume at least one constant-sensitivity contour.

By this I mean simply that at least one locus of substantially constant inkdrop-detection sensitivity can be traced within the probe volume. As a practical matter there will ordinarily be a family of many such loci, the number of members of the family most commonly being infinite.

Further the apparatus includes some means for firing through the probe volume, from such a thermal-inkjet pen, inkdrops to be sensed as a variation in the electrical signal from the detector. More particularly, these "firing means" fire inkdrops in a pattern that follows substantially along at least one of the constant-sensitivity contours.

The foregoing may be a definition or description of the third principal aspect or facet of the invention in its most general or broad form, but even in this form it can be seen that the invention enhances the art of inkdrop detection importantly. The beneficial geometrical interrelationship between a pattern of inkdrop nozzles and a pattern of constant system sensitivity tends to provide uniform response of the system to inkdrops anywhere in the nozzle array.

Moreover, through good design practice this feature of the invention can be exploited further to reduce sensitivity of the system to mutual alignment of the pen and the probe volume. The result is additional economic benefit in both manufacturing tolerances and assembly time.

In a fourth of its main independent facets or aspects the invention is apparatus for ascertaining existence of a small particle. This apparatus includes a light source, and a detector for receiving light along a light path from the source—and in response thereto generating a corresponding electrical signal.

Also included is a cylindrical lens, disposed along the light path and cooperating with the source to establish a particle probe volume. The apparatus further includes some means for inserting into the probe volume a particle whose existence is to be ascertained; for reasons suggested earlier, I shall call these the "inserting means".

The preceding two paragraphs may provide a description or definition of the fourth facet of the invention in its broadest or most general form, but even in this form the fourth facet of the invention can be seen to be beneficial for simple, economical detection of very fine particles in a relatively large field. In particular, the use of a cylindrical lens is an extremely inexpensive way to funnel light from a particle probe volume into a small beam—a beam which is ideally suited for optoelectronic detection with minimal alignment requirements or other fussy arrangements.

In a fifth of its major facets or aspects, the invention is apparatus for ascertaining existence of a small inkdrop ejected from a thermal-inkjet pen. The apparatus includes a lamp at one end of a light path; this lamp provides a nonpoint light source having an extended, threadlike form approximately perpendicular to the light path.

The apparatus of this fifth main aspect of the invention also includes a detector for receiving light through the light path from the source and in response thereto generating a corresponding electrical signal. Also included is an optical element for receiving light from the source through an inkdrop probe volume and for causing light that passes through the inkdrop probe volume to also be concentrated for passage to the detector. The apparatus also includes some means for firing through the probe volume, from such a thermal-inkjet pen, an inkdrop whose existence is to be ascertained.

The above may serve as a definition or description of the fifth main facet of the invention, in its most broad and general form. Even as thus broadly described or defined, however, this fifth aspect of the invention makes an important contribution to refining the inkdrop detection art.

Specifically, use of a transversely extended line source very significantly facilitates the task of defining a large probe volume that is roughly uniform in illumination. Furthermore, with a large probe volume created in this way, light that has passed from the source through the probe volume is readily concentrated or funneled into a narrow beam having favorable properties for detection.

In a sixth main aspect, the invention is apparatus for ascertaining existence of a small inkdrop ejected from a thermal-inkjet pen. The apparatus includes a light source.

The apparatus also includes a detector for receiving light through a light path from the source, and in response thereto generating a corresponding electrical signal. In this sixth facet of the invention, the detector has a cross-section that is substantially longest along a particular dimension transverse to the light path.

The detector also has sensitivity to light that is approximately independent of position along that longest particular dimension. More rigorously speaking, the light sensitivity is approximately position-independent at least within a portion of the longest particular dimension.

The apparatus also includes some means for passing light from the source to the detector through an inkdrop probe volume and for causing light that passes through the inkdrop probe volume to also be concentrated for passage through a beam volume, along a segment of the light path. The cross-section of this beam volume is much smaller than the cross-section of the probe volume.

The size of the beam-volume cross-section is longest in a particular direction transverse to the light path. Further, the intensity of the light is, within the above-mentioned segment, approximately independent of position —both along the light path and along the longest particular direction.

The apparatus also has some means for firing through the probe volume, from such a thermal-inkjet pen, an inkdrop whose existence is to be ascertained.

In preferred embodiments of this sixth main aspect of the invention, the detector is:

(a) disposed to intersect the beam volume within the position-independent-intensity segment, and (b) oriented with its longest particular dimension substantially perpendicular to the longest particular direction of the beam-volume cross-section; and (c) positioned so that the position-independent-sensitivity portion of its longest particular dimension intersects the position-independent-size-and-intensity segment of the longest particular direction of the light-beam volume cross-section.

In consequence of this arrangement, the system is, in the first order, insensitive to dimensional tolerances—and alignment precision as well. I refer to positional tolerances and alignments of the detector and the light-passing-and-concentration-causing means—both longitudinally along the light path and also transversely—in relation to each other.

As mentioned earlier, even though these several main aspects of the invention are amenable to use independently, for optimum enjoyment of all the benefits of the invention these aspects of the invention are best all practiced together. Also the invention is best practiced in conjunction with certain other features or characteristics that further enhance its benefits. For example, preferably the light-passing-and-concentration-causing means include means for causing the beam-volume cross-section to pass through a minimum (that is, minimum dimension in at least one direction), within the segment mentioned previously; and the detector is disposed to intersect the beam volume approximately at that minimum It is also preferable that the inkdrop probe volume section through which the firing means cause inkdrops to be fired be a longitudinal section; and that this longitudinal section exceed an area that encompasses all nozzles of such thermal-inkjet pen. For most geometries, a longitudinal section along the system axis—of the several section orientations mentioned earlier—offers best simplicity, detection sensitivity, and independence of tolerances and alignments.

I also prefer that the firing means include means for repetitively firing a selected nozzle multiple times; and that the apparatus further include signal-receiving-and-processing means for:

receiving the signal from the detector, associating the received signal with a particular operation of the firing means to fire an individual inkdrop from a selected nozzle, storing a time sequence of the signal associated with an individual inkdrop from the selected nozzle, and combining a multiplicity of stored signal time sequences associated with respective individual inkdrops from the selected nozzle to obtain a composite signal representative of inkdrops generally, from the selected nozzle.

In addition it is preferred that the system be designed for use with at least four pens that have different nozzle footprints respectively; and that the section mentioned above exceed the nozzle footprint of each one of all four pens. One relatively simple way to satisfy this condition is to make the section exceed each footprint in each of two orthogonal directions; however, this is not a requirement, and the longitudinal or other section may instead have a carved sort of configuration that accommodates all the pens of interest but does not accommodate a generalized area defined by the extreme dimensions of all pens of interest.

It is also preferable that the constant-sensitivity contour—mentioned above in relation to the third main aspect of the invention—approximate, within a selected segment, the shape of a nozzle array of such a thermalinkjet pen. In this instance it is also preferable that the firing means include some means for holding such a pen with its nozzle array approximately parallel to the constant-sensitivity contour within the selected segment. (A result is to actualize the potential benefit of essentially uniform response to all the nozzles of the array.)

Thus preferably when the apparatus is for use with a pen whose nozzles are arrayed in two parallel substantially rectilinear rows, then it is preferred that at least one constant-sensitivity contour correspondingly approximate, within selected segments of such contours, a pair of parallel planes.

Alternatively it is preferred that at least one constant-sensitivity contour be an oblong shape having a long axis centered along and parallel to the light path, and having substantially symmetrical opposite sides that are, within selected segments, generally parallel to the light path. For still other configurations it is preferred that at least one constant-sensitivity contour intersect, and be interrupted by, the light source.

In yet other geometries it is preferred that at least one constant-sensitivity contour be spaced away from both the probe-volume defining means and the adjacent terminating element, and include an uninterrupted closed figure. In still another favored geometry, the probe-volume defining means also establish within the probe volume at least one approximately constant-sensitivity area.

I also prefer that the cross-section of the light-beam volume within the previously mentioned segment (the segment within which that cross-section is approximately independent of position along the light path) be substantially longer in a first direction transverse to the light path than in a second direction which is also transverse to the light path but at right angles to the first direction. In the same context it is preferable that the detector have a cross-section that is substantially longer along a first particular dimension transverse to the light path than in a second particular dimension transverse to the light path and at right angles to the first particular dimension; and that the detector be oriented with its first particular dimension substantially perpendicular to the first particular direction of the light-beam volume cross-section.

In thermal-inkjet applications I also prefer that the firing means or inserting means, as the case may be, include some means for holding a thermal-inkjet pen with its ink-ejecting nozzles in position to fire inkdrops through the probe volume. I further prefer that the inserting means include some means for actuating the pen to fire inkdrops while the holding means hold the pen with its nozzles in that position.

Further still I prefer to include some means for establishing which nozzles of the pen are fired; and some means for correlating information from the nozzle-establishing means with information from the detector, to derive therefrom information about firing capabilities of individual nozzles respectively.

All of the foregoing operational principles and advantages of the present invention will be more fully appreciated upon consideration of the following detailed description, with reference to the appended drawings, of which:

BRIEF DESCRIPTION OF THE DRAWINGS

FIG. 9 is a perspective or isometric drawing, taken from slightly below the optical path, showing the main optical and mechanical elements of the system—and an inkjet pen to be tested—all roughly to scale.

DETAILED DESCRIPTION OF THE PREFERRED EMBODIMENTS

1. OPTICAL LAYOUT

Figure 1:
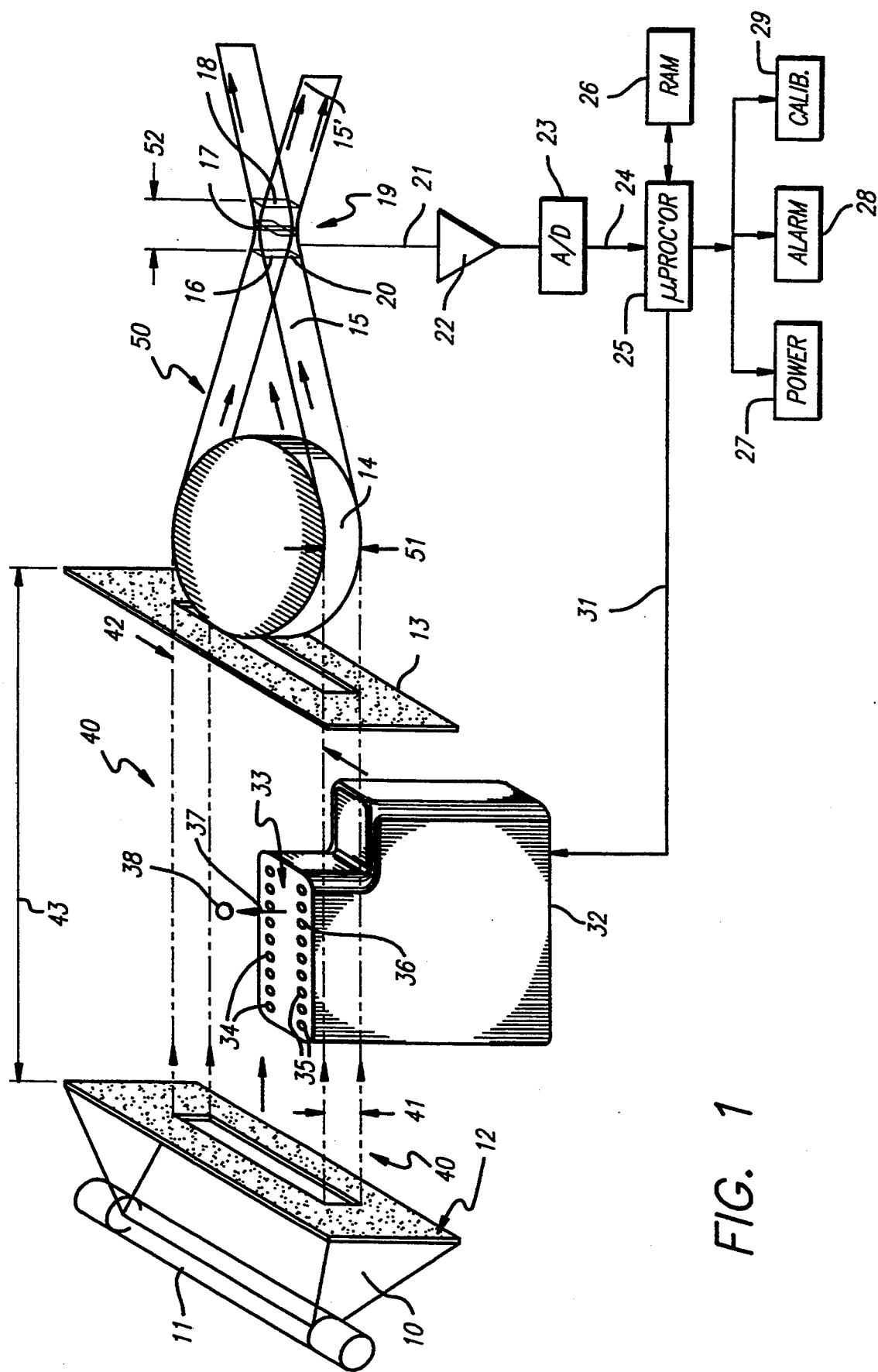
FIG. 1 is a perspective or isometric view of the optical system of a preferred embodiment of the invention, with a representative thermal-inkjet pen operationally juxtaposed.

In preferred embodiments of my invention, light 10 originates in a source 11 (FIGS. 1 and 9) that is thread-like in shape—the "thread" being transverse to the light path—and proceeds to a cylindrical lens 14. The light source 11 may be any of a great variety of ordinary lamps, such as for example bulbs commonly used in automotive environments for some so-called "dome lights". The source 11 and lens 14 together generally define a probe volume 40, though if desired additional aperture screens 12, 13 may be provided as suggested in FIG. 1.

Inkdrops 38 (shown exaggerated in size) preferably are fired—provided, of course, that the nozzles 34, 35, 36 do in fact work—vertically through the probe volume 40 from an inkjet pen 32 immediately above. (In FIG. 1, for convenience of schematic illustration only, the pen 32 has been drawn as below the probe volume 40, but as will be understood such an arrangement would be disadvantageous as ink would fall back through the probe volume 40, causing a second optical disturbance and also possibly spreading over the nozzle plate and nozzle array 33 and so interfering with later operation of the pen.)

It is important that the probe volume 40, or some sensitive or otherwise selected operational portion of the probe volume, be large enough to accept inkdrops from the entire nozzle array 33 of any pen 32 to be tested. Otherwise a positioning mechanism would be necessary to align the operational portion of the probe volume 40 with each nozzle 36 to be tested.

In principle the pen carriage of an inkjet printer might be employed as such a positioning mechanism. The added complexity and certain uncertainties introduced by such an arrangement, however, militate in favor of holding each pen 32 stationary in a single common position, relative to the probe volume 40, while testing all the nozzles 34-36 of that pen.

It is also very desirable that the change of total light flux 50 (directed toward the detector) due to passage of a single inkdrop 38 through the probe volume 40 be reasonably independent of the location of the trajectory 37 of that drop 38. Otherwise, certain nozzles that actually produce unacceptably small drops might be classified as operating properly, and conversely.

The cylindrical lens 14 collects light 10 from the entire probe volume 40 and concentrates it into a beam volume 19 that has a very generally constant height 41, 51 18 and, considered in two horizontal dimensions, a narrow waist. In FIG. 1 the "beam volume" 19 is defined as that volume which is (1) within the transverse envelope 50, 15, 15' of the beam and (2) between two tall, narrow cross-sections or planes 16, 18 that are respectively just upstream and just downstream of the similarly shaped exactly-central plane 17 of the waist.

The light-sensitive surface 20 of an optoelectronic detector such as a light-sensitive diode 21' (FIG. 9) is disposed at the waist to intercept part of the beam. As will be seen, the detector sensitive surface 20 is elongated in a direction transverse to the light path.

The beam waist generally resembles the central portion of an hourglass shape 15, 15', specifically in that it reaches a minimum width at the central plane 17 but then diverges—to the extent, naturally, that it is not intercepted by the detector 20. At and near the minimum width, the beam waist is considerably narrower than the beam height (which is to say, roughly, the lens height 51).

Thus in this region the beam constitutes a bright, narrow bar 16, 17, 18 of light that is vertical (i.e., parallel to the lens 14 axis). As the two sides of the hourglass shape 15, 15' are roughly parabolic, if a good choice of lens 14 diameter is made they provide rather smooth, shallow curvatures of the beam envelope both upstream 15 and downstream 15' from the minimum-width plane 17.

For instance the beam width may diverge by no more than five percent over a longitudinal excursion of 2 mm (1/12 inch), or fifteen percent over a longitudinal excursion of $3\frac{1}{2}$ mm (1/7 inch), in either direction from the minimum. The overall length of this width-insensitive region 19 is thus 4 to 7 mm, and placement of a detector plane 20 within such a length is, respectively, easy and extremely easy.

A fifteen-percent variation of the beam width and therefore detector-signal strength, relative to nominal, is significant in comparison with noise sources in the detection system. Nevertheless that magnitude of departure from nominal width is acceptable if the detector is secured firmly in place, so that the fifteen-percent departure is itself constant—provided that the detector 20 signal is processed through an automatic gain control or other means for accommodating relatively high or low signal strength.

A five-percent variation of beam width is likely to be lost in detection-system noise and so is even more clearly inconsequential; yet a still tighter range of positions, as for example 1 mm in either direction from the central plane 17, with a corresponding beam-width divergence of one or two percent, is entirely feasible from the standpoint of production-line alignment procedures. For purposes of my invention, that degree of care may be seen as relatively undesirable if it can be avoided without penalty; on the other hand, the additional signal range to be accommodated with the slightly higher percentage variation associated with "easy" placement may make the "easy" placement correspondingly slightly less desirable.

Therefore, as between these three values of detector-placement tolerance, the choice becomes a matter of conventional engineering tradeoffs. These alternatives considered together provide a definition of the condition mentioned earlier, for the first two main aspects or facets of the invention, of approximate position-independence for the beam-volume cross-section.

Thus these three distances, $\pm 1$, $\pm 2$ and $\pm 3\frac{1}{2}$ mm, may be taken as alternative preferable values for the length 52 of the previously discussed "beam volume" 19, or the "segment" within which—for easiest, quickest and least expensive assembly—the nominal detector position 20 should be selected; and the corresponding beam divergences of about one or two percent, five percent and fifteen percent respectively serve as alternative definitions of the condition that "within at least that segment, the beam-volume cross-section is approximately independent of position along the light path."

As will now be clear, at least in a first-order approximation within such a segment 19, 52 of the light path the beam cross-section 16, 17, 18 is indeed effectively independent of position along the path. As will be appreciated this arrangement confers upon the system an extraordinarily favorable insensitivity to precision of detector 20 placement along the optical path 10, 50, and thereby renders optical assembly and alignment extremely easy, quick and inexpensive.

As will be understood, other optical-element types may provide generally similar optical behavior and their use is within the scope of certain of the appended claims. For extreme economy and ease of use, however, I prefer a circular-cylindrical lens 14 and ideally one made by simply cutting a wafer, roughly 8 mm ($\frac{1}{3}$ inch) tall from a circular-cross-section rod of inexpensive plastic such as clear acrylic, with diameter about $2\frac{1}{2}$ cm (1 inch).

From the way in which the lens 14 is used in my invention, and in particular the preferred firing of inkdrops 38 through the probe volume 40 parallel to the lens axis, the illumination in the beam volume 19 is very nearly uniform as evaluated along the beam height 51—near the center of that height. This near-uniformity fails near the top and bottom of the beam volume—disrupted by penumbral effects due to shallow vertical divergence of the beam 15, 15', and edge effects from the lens 14 itself.

By selecting a lens 14 of adequate thickness (or height, as in the drawing) 51, however, the nearly-uniform central portion or segment 53 (FIG. 2) of the beam height 51 is easily made quite tall—limited, to an extent, by need for some corresponding vertical extension of the horizontally "threadlike" source. I have found that, with lens 14 dimensions as mentioned above, the roughly position-independent central segment 53 of the beam height can be made about 5 to 9 mm tall—again, as in the foregoing discussion of longitudinal alignment requirements, the exact value being associated with some selection of a percentage variation that can be regarded as "position independent".

I prefer to use a detector 20 whose light-sensitive area is elongated transversely to the light path, with width much smaller than the height 51 of the lens 14 and therefore the height of the beam volume 19. The detector 20 should be reasonably uniform in response, at least along a segment 54 (FIG. 2) of its elongated dimension.

The detector 20 should be oriented with its transverse elongation at right angles (FIGS. 1 and 2) to the transverse elongation of the beam volume 19, and positioned so that the uniform-response segment 53 of the detector 20 intersects 55 the central, uniform-illumination segment 54 of the beam-volume height 51. Only this intersection area 55 of beam 19 and detector 20 produces an electrical output signal 21; the unlit areas 56 of the detector 20 outside this intersection 55 do not contribute.

With these conditions met, the signal-producing intersection 55 rests at a three-dimensional detection-sensitivity saddle, such that displacement of the detector 20 in any direction—while it may move the intersection 55 along the detector 20—maintains very nearly the same size, shape, and illumination intensity of the intersection 55; and so very nearly the same electrical output signal 21.

Furthermore the output is insensitive to small rotations, too, of the detector—if the detector is nominally positioned so that the light path is normal to the sensitive area of the detector. This is so because, at normal incidence, the intersection area as a function of angular position—both within the plane of FIG. 2 and out of that plane—also has minima.

By virtue of these several independence conditions, the system is insensitive to a wide range of manufacturing tolerances, alignment imprecisions, and possible disturbances during use.

As FIG. 1 shows, a system according to my invention also preferably includes a preamplifier 22 for producing an analog signal proportional to the photodetector analog signal 21 but of lower impedance, an analog-to-digital converter 23 for receiving the lower-impedance signal and producing a corresponding digital signal 24, and a microprocessor 25 for receiving and interpreting these digital data 24. As a practical matter the microprocessor 25 may be one and the same with a microprocessor that operates 31 the pen 32 and the rest of the printing machine—or other apparatus with which the detector 20 is associated.

Whether a single processor 25 or several processors are used, the processor that receives the detection-apparatus data must be coordinated with the processor that selects and fires 31 the pen nozzles 34–36, so that the information derived from operation of the detection apparatus can be usefully applied. This information may be used to automatically control later operation 31, 27 of the pen and printer, or to alert 28 a human operator to inadequate pen performance, or for positional calibrations 29, or otherwise.

2. OPTIMIZING USE OF THE PROBE VOLUME

Various parameters influence the strength of the detector output signal. The most important are:
illumination brightness and uniformity,
probe-volume 40 aperture widths 42 and heights 41,
probe-volume length 43,
lens 14 diameter and refractive index,
drop 38 cross-section, and
detector 20 sensitivity.

For good performance all of these factors must be given careful attention, in accordance with good optical design practice. To avoid undesired positional variation of signal 21, 24, neither the lamp 11 nor any spatial surface within the probe volume 40 should be focused on the detector 20.

Figure 2:
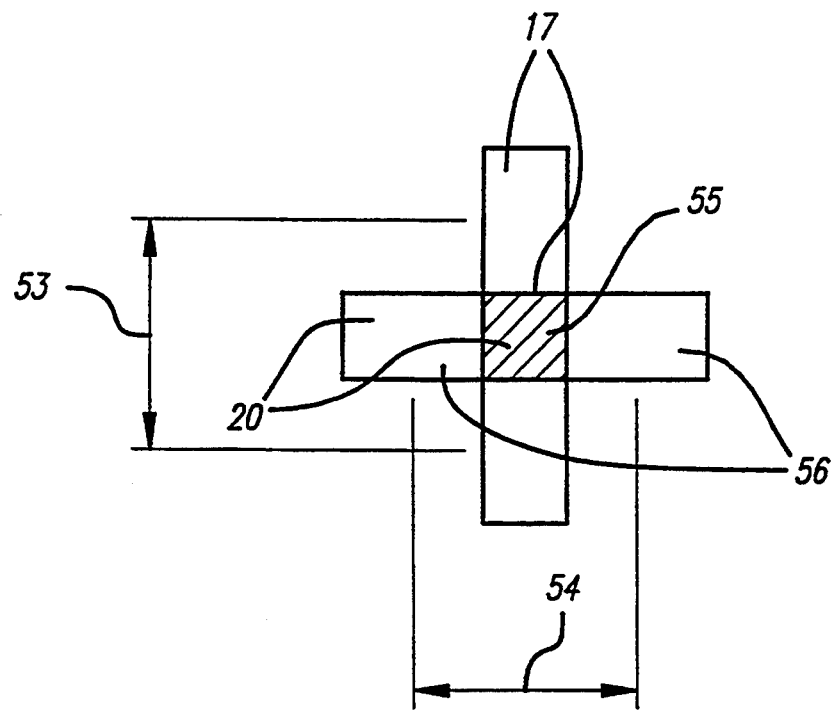
FIG. 2 is a somewhat schematic cross-sectional view of the light beam and the active area of the detector, taken across the plane 2—2 in FIG. 1.
Figure 3:
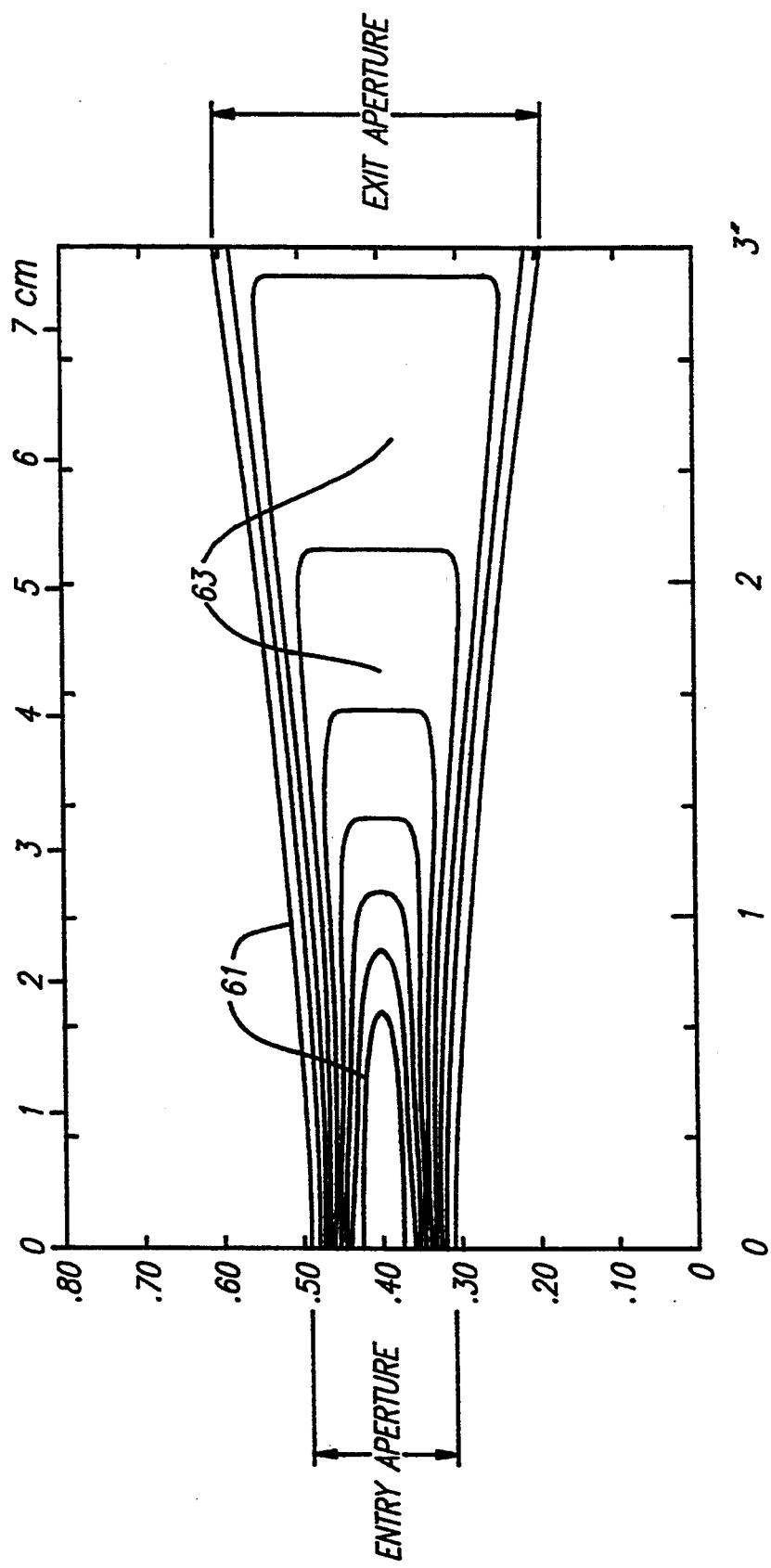
FIG. 3 is a plan view of the FIG. 1 probe volume, showing a computer-generated family of constant-system-sensitivity contours for one specific configuration of the optical system as described in a later section of this document.

Special attention should be given to the probe-volume width 42 and length 43, as the system of FIGS. 1 and 2 will be found to exhibit important sensitivities to these factors—and in particular to placement of an ink-drop 38 or other occulting particle widthwise and lengthwise within the probe volume 40. FIG. 3 shows such variation of relative sensitivity for one representative drop-detecting device.

For demonstration purposes the sensitivity scale is arbitrary. The diagram depicts lines in a plane that is part of the probe volume and stretches from one aperture to the other (or from lamp 11 to lens 14); the plane is parallel to the long axes of the apertures and contains the optical axis or centerline of the system.

Each line 61 in the diagram connects points in this plane at which the sensitivity of the drop detector is equal to some fixed value—a different value for each line. In short, these are lines of constant sensitivity.

Since the detection sensitivity will be very nearly constant along the direction parallel to the lens axis these constant-sensitivity contours 61 actually represent surfaces of constant sensitivity. (Where such lines 62 form closed shapes as in FIG. 5, these constant-sensitivity surfaces are correspondingly cylindrical, though not circularly cylindrical.)

FIG. 3 may be understood as a plan view of the central plane in the probe volume 40. To the left is the lamp 11 or entry aperture, width 5 mm (0.2 inch); and to the right, the lens 14 or exit aperture, width 1 cm (0.4 inch). The intervening distance, the length 43 of the probe volume, is about 7½ cm (3 inches).

The sensitivity contours, then, predict the relative strength of the detector signal 21 as a small particle 38 of given size is moved from place to place within the probe-volume 40 central horizontal plane. Guided by the present document and with the aid of ordinary computer techniques used in optical systems, a skilled designer can straightforwardly generate this type of diagram for a great variety of probe-volume geometries.

Study of such diagrams will be found very helpful in determining where and how to best define and juxtapose a probe volume 40 to a particular thermal-inkjet pen 32 or pens, or other particle 38 source—or how to best convert a preexisting particle-prone volume of interest into a particle probe volume for application of the principles set forth in this document. In most cases it will be found that there is no single optimal design.

Certain system attributes, however, are very desirable and can be implemented with the described arrangement through suitable choice of probe-volume dimensions. Such attributes include:

virtually equal sensitivity for all nozzles 34–36 that are arranged in two columns parallel to the optical axis;

adaptability to column pairs 34, 35 with a wide variety of mutual distances; and relatively free choice of the aperture 12, 13 locations in relation to the nozzle columns 34, 35 (that is, to a pen 32).

The first-listed attribute is generally easy to achieve because the constant-sensitivity contours 61, 62 at various locations approximate straight lines quite well. The last-listed can be important when it is desired to keep the apertures 12, 13 well away from the nozzles 34–36, to minimize mechanical interferences.

Figure 4:
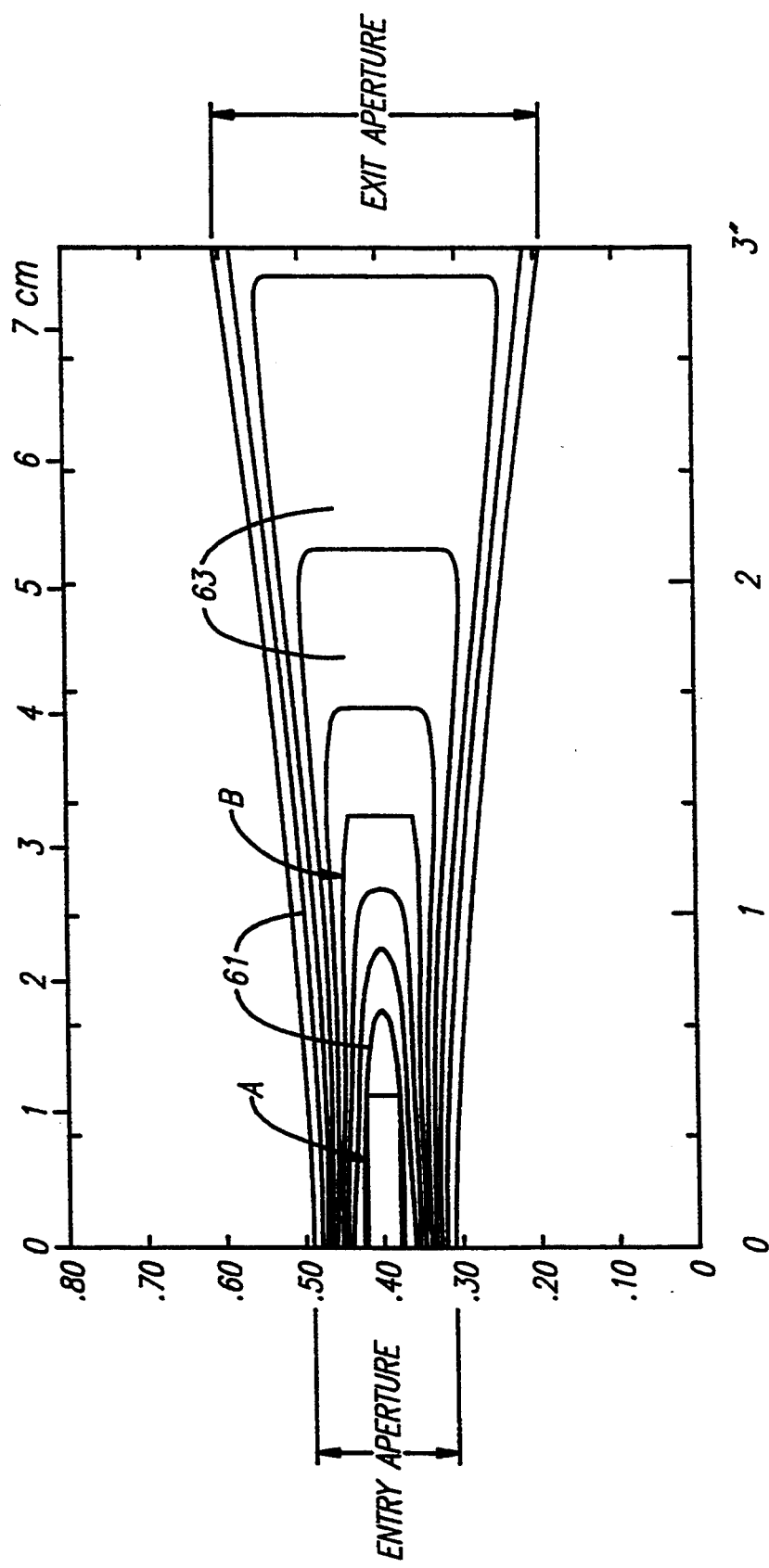
FIG. 4 is a like view having superposed certain alternative preferred positions of the pen nozzle array.

All three of these attributes are demonstrated by the approximately rectangular traces A and B in FIG. 4, where the longer sides depict the lengths and locations of the nozzle columns 34, 35 for best performance of the detection system. Trace A represents optimal nozzle location for a pen with two nozzle columns 34, 35 of length approximately 1¼ cm (0.4 inch) or less, spaced apart approximately 1¼ mm (1/20 inch). Similarly trace B represents optimal nozzle location for a pen with columns 34, 35 of length about 3 cm (1.2 inch) or less, and separation about 2 mm (0.08 inch).

Both traces A, B are, in this case, immediately in front of the entry aperture 12—i.e., just downstream from the lamp 11. This is a consequence of the fact that in FIG. 3 the entry aperture 12 (cf. FIG. 1) is smaller than the exit aperture 13 (specifically, 5 vs. 10 mm).

The relatively larger coverage indicated for trace B is obtained at the cost of a roughly thirty-percent reduction in sensitivity. Other useful insights concerning the characteristics of this system can be gleaned from study of the drawing; for instance, roughly uniform-sensitivity areas can be found in regions of the probe-volume central plane where the constant-sensitivity contours are spaced relatively far apart—notably the right-central parts 63 of the diagram.

Figure 5:
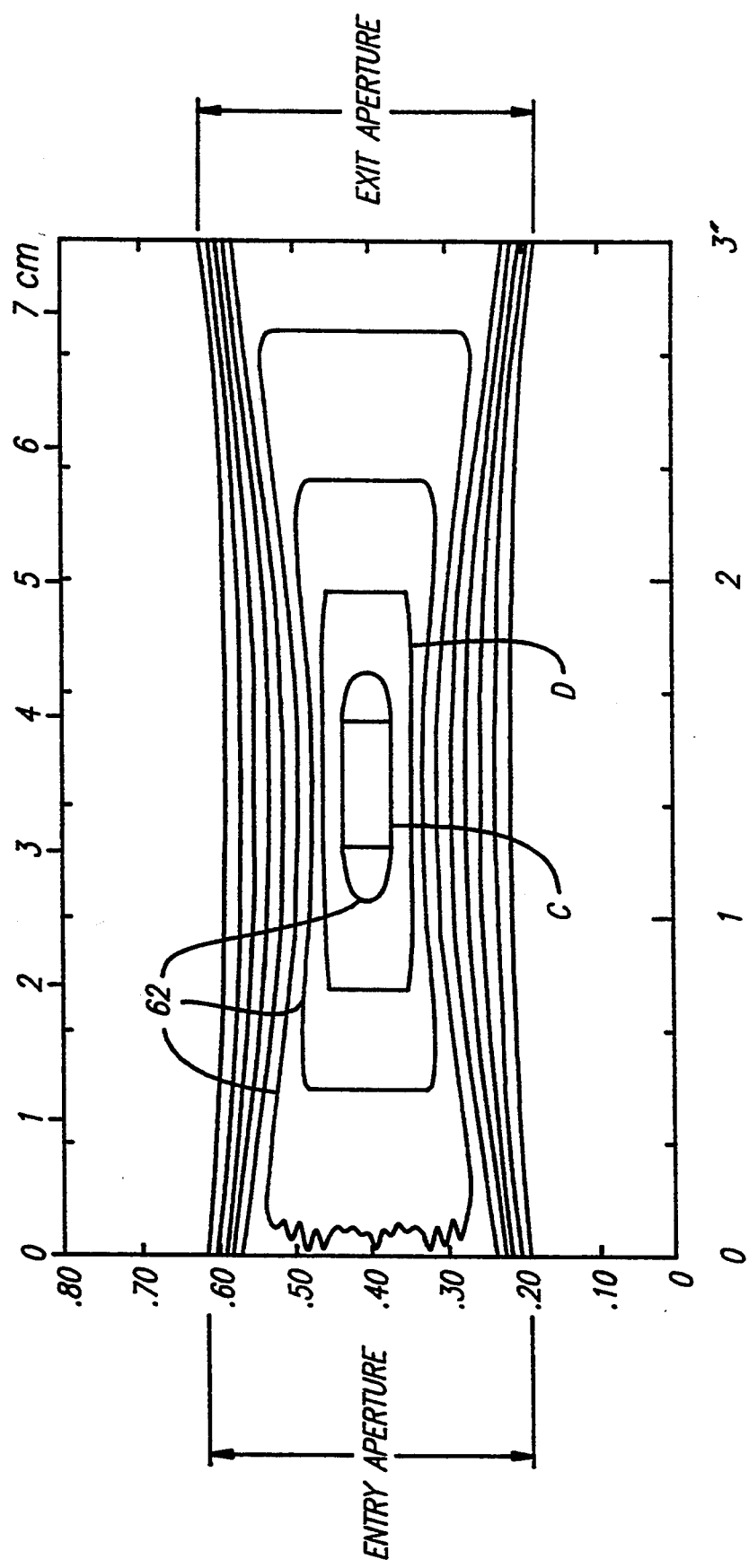
FIG. 5 is a plan view similar to FIG. 3 but for a different specific configuration of the optical system, as also described later in this document.

In contrast to the rearward-skewed sensitivity concentrations 61 produced by the aperture size differential of FIGS. 3 and 4, a symmetrical layout of isosensitivity contours 62 can be obtained through use of equal apertures —as in FIG. 5, where both exit 13 (FIG. 1) and entry 12 are 10 mm wide. Here the loci 62 of constant sensitivity are centered in the probe-volume central plane.

Possible pen positions, distinguished by their close approximation to rectangles, are superposed. Trace C indicates the location of a hypothetical pen with two columns of nozzles as long as 7½ mm (0.3 inch), and separated by 1½ mm (0.06 inch). Trace D represents the location of another hypothetical pen whose two columns are up to 25 mm (1 inch) long and 2½ mm (0.1 inch) apart.

Figure 6:
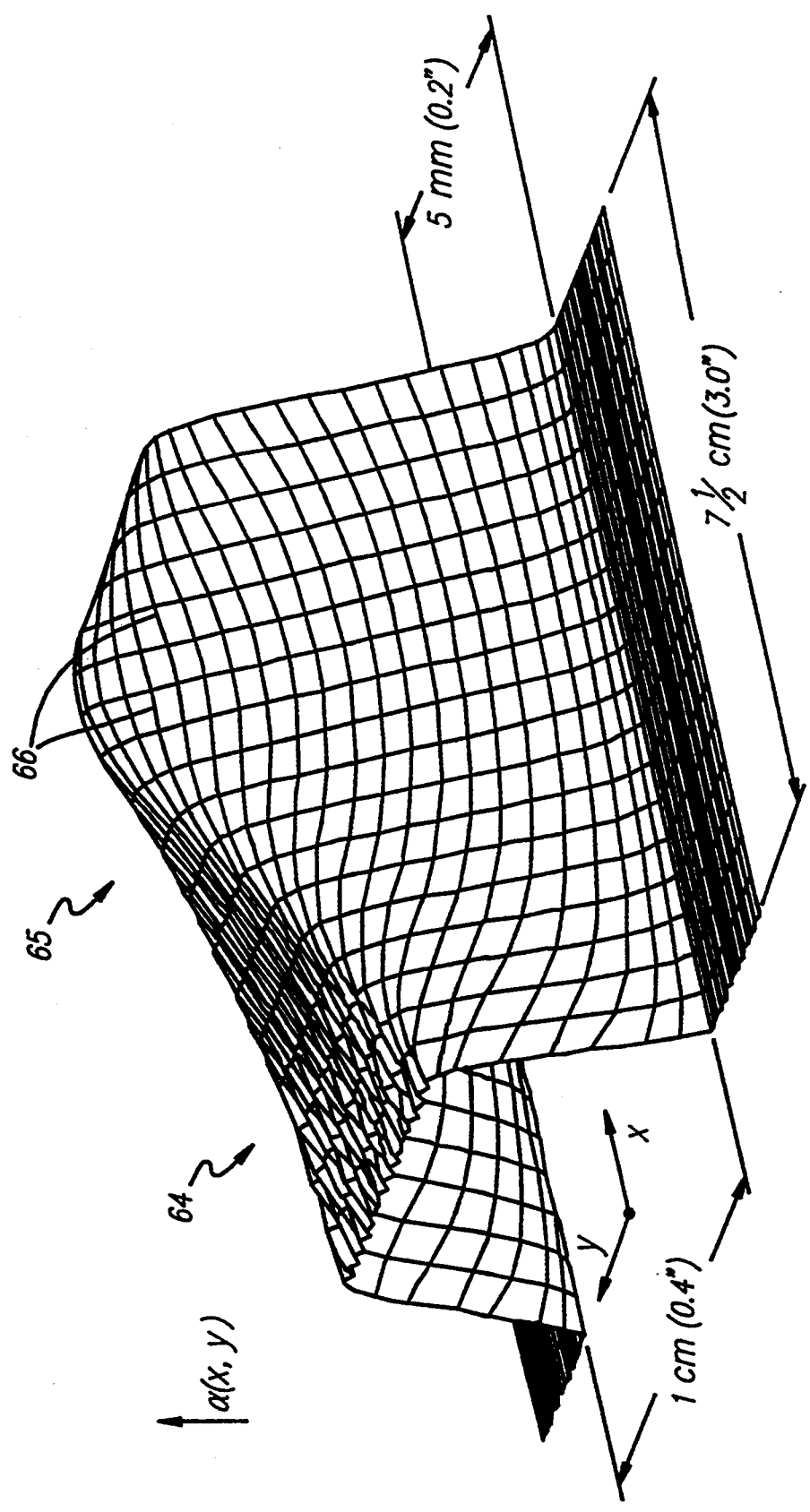
FIG. 6 is an computer-generated isometric-appearing view of a three-dimensional graph of detection sensitivity, for an optical-system configuration that is very generally like those of FIGS. 3 through 5.

The way in which the sensitivity contours 61, 62 of FIGS. 3 through 5 arise can perhaps be more intuitively conceptualized through study of FIG. 6. This is a simulation of the magnitude of light-flux change $\alpha$ as a function of location x, y, of inkdrop passage through a probe volume formed by a lamp 11, lens 14 and detector 20 as previously outlined.

The left side (x=0) adjoins the bulb 11, the right side (x=7½ cm) the lens; and the z (vertical) axis is parallel to the inkdrop trajectories—and is at any point x,y a measure of the sensitivity $\alpha$. (In FIG. 6 different scales are used for the and axes.) This function $\alpha(x,y)$ accordingly arises from a choice of relative aperture sizes which is opposite to that of FIGS. 3 and 4, as here the entry aperture 12 (FIG. 1) is twice as wide as the exit aperture 13.

Very evidently this function varies significantly over the entire area—with a sharply narrow peak paralleling the optical path (E axis). Nevertheless zones can be selected that are very usable for purposes of the invention: there is a larger, rather flat zone 64 next to the bulb 11 (rather than at 63 next to the lens 14, as in FIG. 3), and there are mutually parallel ridge lines 66 of nearly constant sensitivity straddling the peak 65.

These features are readily associated with corresponding features of the planar-section presentations in FIGS. 3 through 5. The above-discussed uses, too, of these same features may be understood directly from the three-dimensional FIG. 6 graph.

Thus if the optical path is laid out properly the nearly flat part 64 of the $\alpha(x,y)$ function provides a rather large, if somewhat insensitive, zone of almost constant sensitivity. On the other hand, if the pen nozzles happen to be arranged in two columns 34, 35, the pen 32 can be positioned so that these columns 34, 35 are aligned with the ridge lines 66 of nearly constant sensitivity —thereby providing a response that is both high and in effect nearly uniform over the nozzle array 33.

As to the designated ridge lines 66 in the drawing, it will be noted that below these particular lines of constant y value the other constant-y parallels appear to be upward-concave, and above them convex. Hence the designated ridge lines 66 (and other parallels between or immediately adjacent) appear most nearly constant in sensitivity $\alpha$.

More particularly, the lower of the two designated ridge lines 66 may seem very slightly undulating in elevation $\alpha$, yet very nearly constant in that parameter over a relatively long extent; while the upper of the two may seem slightly more straight or constant in $\alpha$ but over a shorter distance. Thus depending upon the length of the nozzle array one or the other of these two lines of constant y value, or any intervening or immediately adjacent ones, will serve well.

Many other useful configurations of this invention can be found by studying the probe-volume sensitivity profiles associated with various probe-volume aspect ratios. Designs can be scaled up and down to better accommodate given pens.

Figure 7:
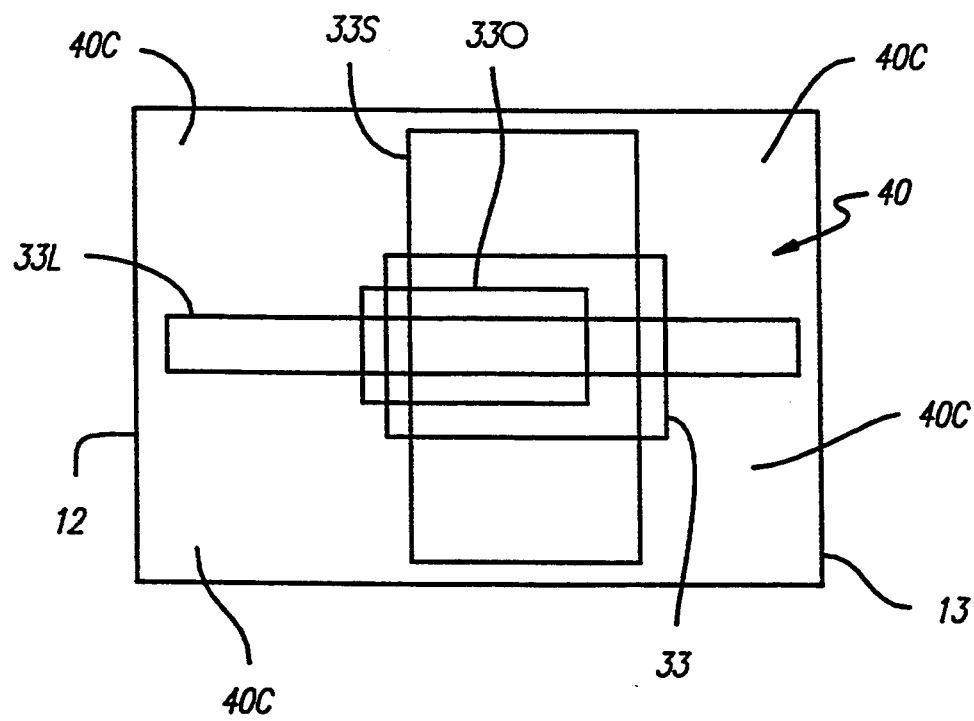
FIG. 7 is a schematic plan view of an inkdrop or particle probe volume analogous to FIGS. 3 through 5 but showing different ways in which the probe-volume section can exceed different nozzle footprints of different pens.

FIG. 7 shows very schematically how multiple pens having different footprints may be accommodated by a single probe volume in common. In this drawing no attempt is made to take account of sensitivity contours discussed above.

In FIG. 7 a long slender array 33L of nozzles, a short broad array 33S of nozzles, and two other arrays 33, 330 of nozzles are all shown disposed for discharge of inkdrops through the probe volume 40. It will be understood that ordinarily only one pen at a time will be so positioned.

The probe volume 40 of FIG. 7 accommodates all these differing pen dimensions by having a usable length that is at least as long as the length of the longest nozzle array 33L, and a usable width that is at least as long as the width of the widest nozzle array 33S. For use in a printer that works with these several pens all installed at the same time and to be tested without realignments of the optical system etc., the detection system will be best designed to use some such sensitivity plateau 64 in FIG. 6, or 63 as shown in FIGS. 3 and 4, even though detection sensitivity is relatively low.

In this sort of system, making the usable length and width large enough for every nozzle array may in a sense constitute a somewhat brute-force approach. Perhaps for such multipen applications a probe volume whose usable regions exclude, for example, the extreme corners 40C—to which none of the nozzle arrays 33, 33L, 33S, 33O of interest happens to extend—may be more effective, or more cost-effective.

If, however, the inkdrop detection system is for use in any of several different printers, each of which works with only one of the pen footprints 33, 33S, 33L, 33O, then the system as installed on each printer may preferably be optimized for each corresponding pen, respectively. In this case it may be more attractive to align pen nozzle rows with sensitivity-function ridge lines 66, to optimize the detection system for the specific pen with which it is to be used.

As will now be clear the ideal use of my invention encompasses construction and study of straightforward detection-sensitivity analyses such as those introduced in this document. Such analytical construction and study will guide the designer in adaptation and optimization of both a sensitivity function $a(x,y)$ and a particle-source placement geometry to the problem at hand.

3. SIGNAL ANALYSIS

Figure 8:
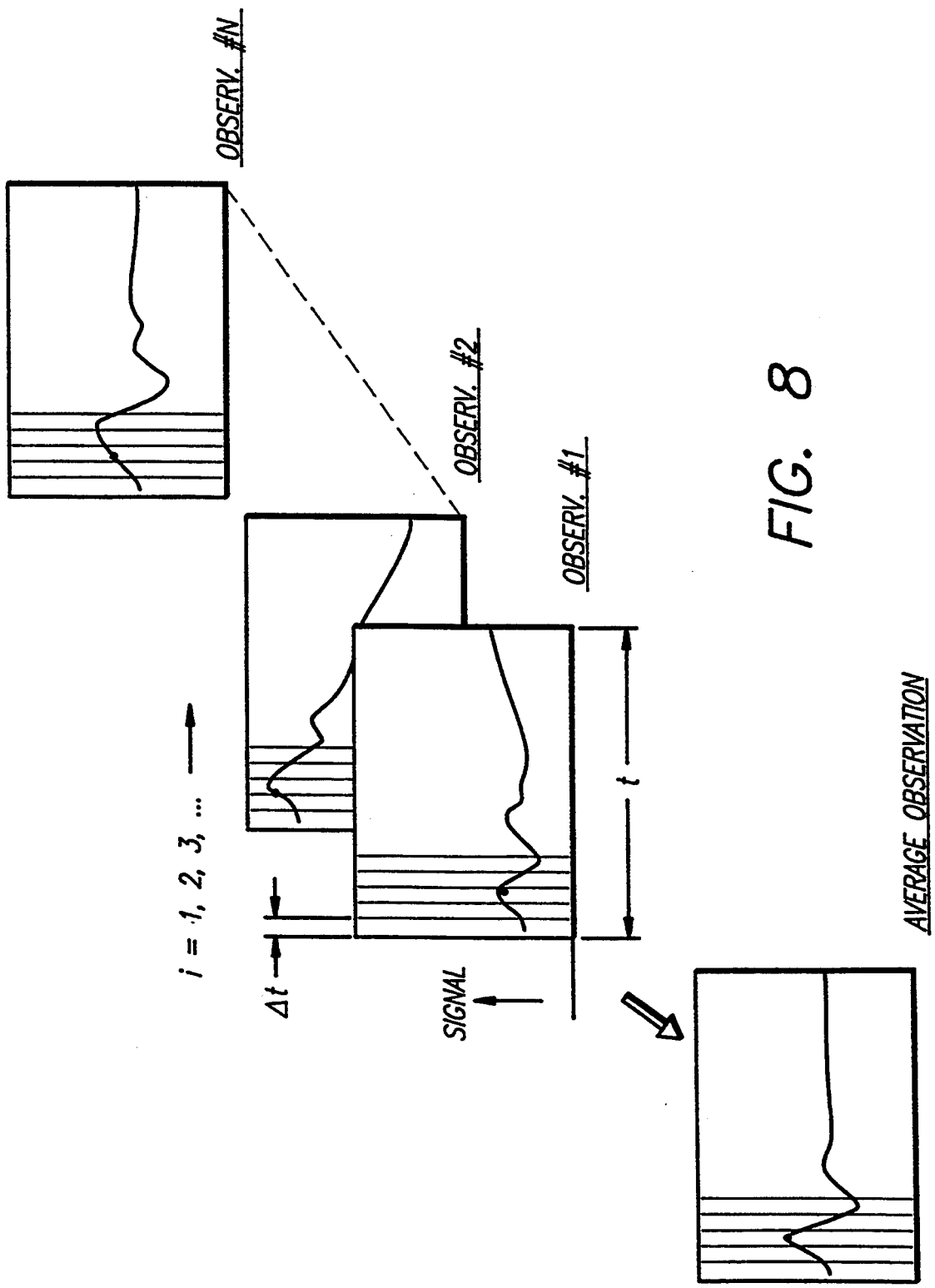
FIG. 8 is a set of representative signal diagrams showing how processing of electronic signals from the FIG. 1 detector can be optimized to obtain a drop-detection signal with high signal-to-noise ratio.

FIG. 8 illustrates the algorithm which I prefer for separation of the signal proper from unavoidably associated noise. In a microprocessor-controlled printing machine, this algorithm is relatively simple to implement using an analog-to-digital converter 23 connected to the microprocessor 25 that controls it and the rest of the printer.

I shall first describe operation of the pen 32 and the inkdrop detector 11-14-19-20-22-23 together. Upon a command to the pen, a nozzle 36 ejects an inkdrop 38; after a delay of about 100 $\mu$sec the drop 38 enters the probe volume 40 and so dims the light 10, 50 passing through that volume.

During the entire traversal of the probe volume 40, the drop-detector output current 21 is reduced; then the current 21 is fully restored. This traversal time, too, may be about 100 $\mu$sec.

Because there is a maximum frequency at which a pen can operate, some time—very much longer than 100 $\mu$sec —must elapse before the next inkdrop ejection 37 can occur. FIG. 8 shows, as "observation #1", a trace S1 representing the recorded or stored signal collected while an inkdrop 38 passed through the probe volume 40.

In this trace S1 can be seen the transient 71 caused by the drop, but also distortions and seeming shifts of the baseline 72—which ideally should be just a horizontal line across the center (perhaps) of the recording. The adjacent traces, "observation #2" and generally "observation #n", confirm that the baseline 72 is subject to overall shifts.

A simple trigger set to a particular threshold, say half of the pulse 71 caused by the passing drop 38, would be inadequate to separate valid particle events (inkdrops) from background noise, since the baseline 72 distortions and shifts exceed by far the amplitude of that pulse 71.

The apparatus automatically calculates a single representative record Sa from a sufficient number of individual records S1 ... Sn. Such procedures are well known but in quite different applications such as elimination of noise in oscilloscope displays—for example, in the Model 54502A Digitizing Oscilloscope commercially available from the Hewlett Packard Company.

This algorithm dissects the observation period t for each drop into many short time intervals or slices, all preferably of like width—i.e., all having a common duration. The microprocessor 25 sets aside as many pages of its memory 26 as there will be drops 38 to average, each such page containing as many memory locations as there are time slices in the observation period for one drop 38.

As the measurement proceeds, the microprocessor 25 loads the detector output signal 24, received from the analog-to-digital converter 23 after each time slice, and deposits that signal 24 into the memory 26. This is done in such a way that each page corresponds to one drop 38 observation, and each location within each page corresponds to a particular time slice—the slice that follows the start of the drop-ejection command 31 by a certain multiple of the common slice duration.

After data are thus collected for all the drops, the processor 25 fills one more memory 26 page, again containing the same number of memory locations as in the observation period for each drop 38. Each of these memory locations is filled with the average value for the corresponding time slice for all the drops.

The result is an average sequence Sa for all the observations. In this average the baseline fluctuations 72a diminish—relative to the excursion 71a due to the inkdrops 38.

This signal-to-noise improvement is due to the known premise that correlated signals 71, 71', 71" namely those caused by the drops 38, reinforce each other in proportion to the number of observations taken; while uncorrelated signals, namely noise 72, 72', 72" reinforce only in proportion to the square root of that number. Given a large enough number of drop observations n, the shifts and deformation of the baseline 72a in the average observation Sa therefore can be made as small as desired.

Experiments with a prototype indicated that eight observations would be sufficient, even though the detector apparatus was exposed to stray light from fluorescent lamps in the laboratory. If preferred the detection system can be more elaborately guarded and the number n of observations reduced.

Various methods can be applied to the average-observation data to determine whether a drop signal is present. For instance the peak-to-peak voltage 73 (FIG. 8) or the root-mean-square voltage is usable.

It will be understood that the foregoing disclosure is intended to be merely exemplary, and not to limit the scope of the invention—which is to be determined by reference to the appended claims.

I claim:

1. Apparatus for ascertaining existence of a small inkdrop ejected from a thermal-inkjet pen, said apparatus comprising:
    a light source;
    a detector for receiving light through the light path from the source and in response thereto generating a corresponding electrical signal;
    means for passing light from the source to the detector through an inkdrop probe volume and for causing light that passes through the inkdrop probe volume to also be concentrated for passage through a beam volume, along a segment of the light path, whose cross-section is much smaller than the cross-section of the probe volume and is, within said segment, approximately independent of position along the light path;

said detector being disposed to intersect said beam volume within said segment; and means for firing through the probe volume, from such a thermal-inkjet pen, an inkdrop whose existence is to be ascertained.

2. The apparatus of claim 1, wherein:

the light-passing-and-concentration-causing means comprise means for causing the beam-volume cross-section to pass through a minimum, within said segment; and the detector is disposed to intersect said beam volume approximately at the minimum.

3. The apparatus of claim 1, wherein:

the probe volume has a longitudinal section through which the firing means cause inkdrops to be fired; and said longitudinal section exceeds an area that encompasses all nozzles of such thermal-inkjet pen.

4. The apparatus of claim 1, wherein:

the passing-and-concentration-causing means comprise a cylindrical lens that receives light from the probe volume and concentrates that light into said beam volume.

5. The apparatus of claim 1, for use with such a pen that has a multiplicity of ink-ejecting nozzles:

wherein the firing means comprise means for repetitively firing a selected nozzle multiple times; and further comprising signal-receiving-and-processing means for:

receiving the signal from the detector, associating the received signal with a particular operation of the firing means to fire an individual inkdrop from a selected nozzle, storing a time sequence of the signal associated with an individual inkdrop from the selected nozzle, and combining a multiplicity of stored signal time sequences associated with respective individual inkdrops from the selected nozzle to obtain a composite signal representative of inkdrops generally, from the selected nozzle.

6. Apparatus for ascertaining existence of a small inkdrop, said apparatus comprising:

a plurality of thermal-inkjet pens, each having a respective array of nozzles for ejecting such inkdrops, said plurality of pens including pens having a plurality of different nozzle-array footprints;

a light source;

a detector for receiving light through the light path from the source and in response thereto generating a corresponding electrical signal;

means for passing light from the source to the detector through an inkdrop probe volume and for causing light that passes through the inkdrop probe volume to also be concentrated for passage through a beam volume, along a segment of the light path, whose cross-section is much smaller than the cross-section of the probe volume and is, within said segment, approximately independent of position along the light path;

said detector being disposed to intersect said beam volume within said segment; and means for firing through the probe volume, from at least one of the thermal-inkjet pens, an inkdrop whose existence is to be ascertained;

said inkdrop probe volume having a section through which the firing means cause inkdrops to be fired; and said section exceeds an area that encompasses all nozzles of each one of the plurality of thermal-inkjet pens.

7. The apparatus of claim 6, wherein:

the plurality of thermal-inkjet pens comprises at least four pens with different nozzle footprints respectively; and said section exceeds the nozzle footprint of each of all four pens.

8. The apparatus of claim 7, wherein:

said section exceeds each footprint in each of two orthogonal directions.

9. The apparatus of claim 6, in further combination with:

a thermal-inkjet printing machine that operationally holds, at the same time, at least two of the pens with different nozzle-array footprints.

10. The apparatus and combination of claim 9, wherein said at least two pens with different nozzle-array foot-prints comprise:

a first pen with an array of nozzles for discharging black ink; and a second pen with nozzle subarrays for discharging different colors of ink respectively;

wherein said section exceeds the footprint of the black-ink nozzle array of the first pen, and exceeds an overall footprint that encompasses all the color-ink nozzle subarrays of the second pen.

11. Apparatus for ascertaining existence of a small inkdrop ejected from a thermal-inkjet pen, said apparatus comprising:

a light source;

a detector for receiving light through the light path from the source and in response thereto generating a corresponding electrical signal;

means for cooperating with the source to define an inkdrop probe volume;

sensitivity of said electrical signal to inkdrop existence being variable with respect to inkdrop position within the probe volume;

said probe-volume defining means establishing within the probe volume at least one constant-sensitivity contour; and means for firing through the probe volume and substantially along at least one of said constant-sensitivity contours, from such a thermal-inkjet pen, inkdrops to be sensed as variations in the electrical signal from the detector.

12. The apparatus of claim 11, wherein:

said constant-sensitivity contour approximates, within a selected segment, the shape of a nozzle array of such a thermal-inkjet pen; and the firing means comprise means for holding such pen with its nozzle array approximately parallel to the constant-sensitivity contour within the selected segment.

13. The apparatus of claim 11, for use with such a thermal-inkjet pen whose nozzles are arrayed in two parallel substantially rectilinear rows; and wherein:

at least one constant-sensitivity contour correspondingly approximates, within selected segments of such contours, a pair of parallel planes.

14. The apparatus of claim 11, wherein:

at least one constant-sensitivity contour is an oblong shape having a long axis centered along and parallel to the light path, and having substantially symmetrical opposite sides that are, within selected segments, generally parallel to the light path.

15. The apparatus of claim 14, wherein:
at least one constant-sensitivity contour intersects, and is interrupted by, the light source.

16. The apparatus of claim 14, wherein:
at least one constant-sensitivity contour is spaced away from both the probe-volume defining means and the adjacent terminating element, and comprises an uninterrupted closed figure.

17. The apparatus of claim 11, wherein:
said probe-volume defining means also establish within the probe volume at least one area of approximately constant sensitivity.

18. Apparatus for ascertaining existence of a small particle, said apparatus comprising:
a light source;
a detector for receiving light along a light path from the source and in response thereto generating a corresponding electrical signal;
a cylindrical lens disposed along the light path and cooperating with the source to establish a particle probe volume; and
means for inserting into the probe volume a particle whose existence is to be ascertained.

19. The apparatus of claim 18, wherein:
the cylindrical lens forms, from light reaching the lens through the probe volume, a light-beam volume whose cross-section is approximately insensitive to position along a segment of the light path; and
the detector is disposed to intersect the light-beam volume.

20. The apparatus of claim 19, wherein:
the cross-section of the light-beam volume within said segment is substantially longer in a first direction transverse to the light path than in a second direction which is also transverse to the light path but at right angles to the first direction;
the detector has a cross-section that is substantially longer along a first particular dimension transverse to the light path than in a second particular dimension transverse to the light path and at right angles to the first particular dimension; and
the detector is oriented with its first particular dimension substantially perpendicular to said one direction of the light-beam volume cross-section.

21. The apparatus of claim 18, particularly for ascertaining existence of an inkdrop ejected from a thermalinkjet pen; and wherein:
the inserting means comprise means for holding a thermal-inkjet pen with its ink-ejecting nozzles in position to fire inkdrops through the probe volume.

22. The apparatus of claim 21:
wherein the inserting means comprise means for actuating the pen to fire inkdrops while the holding means hold the pen with its nozzles in said position, and means for establishing which nozzles of the pen are fired; and
further comprising means for correlating information from said nozzle-establishing means with information from the detector, to derive therefrom information about firing capabilities of individual nozzles respectively.

23. Apparatus for ascertaining existence of a small inkdrop ejected from a thermal-inkjet pen, said apparatus comprising:
a lamp at one end of a light path, said lamp providing a nonpoint light source having an extended, threadlike form approximately perpendicular to the light path;
a detector for receiving light through the light path from the source and in response thereto generating a corresponding electrical signal;
an optical element for receiving light from the source through an inkdrop probe volume and for causing light that passes through the inkdrop probe volume to also be concentrated for passage to the detector;
means for firing through the probe volume, from such a thermal-inkjet pen, an inkdrop whose existence is to be ascertained.

24. The apparatus of claim 23, wherein:
the optical element has an axis that is approximately perpendicular to the light path; and
the lamp is oriented with its threadlike form also extended perpendicular to the axis of the optical element.

25. The apparatus of claim 23, wherein:
said light concentrated for passage to the detector passes through a light-beam cross-section; said cross-section being longest in a particular direction transverse to the light path;
the cross-section of the light beam has a region, along said longest direction, within which the width of the cross-section and the intensity of said light are relatively independent of position along said longest direction;
the detector has a cross-section that is longest along a particular dimension of the detector, transverse to the light path;
the cross-section of the detector has a region, along its longest particular dimension, within which sensitivity to light is relatively independent of position along said longer particular dimension;
the detector is oriented with its longest particular dimension substantially perpendicular to said longest particular direction of the light-beam cross-section; and
the detector is positioned so that said relatively-independent regions of the light-beam and detector cross-sections intersect.

26. Apparatus for ascertaining existence of a small inkdrop ejected from a thermal-inkjet pen, said apparatus comprising:
a light source;
a detector for receiving light through a light path from the source and in response thereto generating a corresponding electrical signal; the detector having a cross-section that is substantially longest along a particular dimension transverse to the light path, and having sensitivity to light that is approximately independent of position along said longest particular dimension, at least within a portion of the longest particular dimension;
means for passing light from the source to the detector through an inkdrop probe volume and for causing light that passes through the inkdrop probe volume to also be concentrated for passage through a beam volume, along a segment of the light path, whose cross-section is much smaller than the cross-section of the probe volume; the size of the beam-volume cross-section being longest in a particular direction transverse to the light path; and the intensity of said light being, within said segment, approximately independent of position both along the light path and along said longest particular direction; and means for firing through the probe volume, from such a thermal-inkjet pen, an inkdrop whose existence is to be ascertained;

said detector being (a) disposed to intersect said beam volume within said segment, and (b) oriented with its longest particular dimension substantially perpendicular to said longest particular direction of the light-beam volume cross-section; and (c) positioned so that the position-independent-sensitivity portion of its longest particular dimension intersects the position-independent-size-and-intensity segment of the longest particular direction of the light-beam volume cross-section;

whereby the system is, in the first order, insensitive to dimensional tolerances.

* * * * *